(12) United States Patent
Keinan et al.

(10) Patent No.: US 6,271,009 B1
(45) Date of Patent: Aug. 7, 2001

(54) CONTROL OF FRUIT RIPENING AND SENESCENCE IN PLANTS

(75) Inventors: Ehud Keinan, Timrat; Harel Itzhaky, Atlit; Esther Aboud-Pirak, Kiryat Tivon; Shimon Gepstein, Haifa, all of (IL)

(73) Assignee: Vitality Biotechnologies, Inc., Orangeburg, NY (US)

( * ) Notice: Subject to any disclaimer, the term of this patent is extended or adjusted under 35 U.S.C. 154(b) by 0 days.

(21) Appl. No.: 09/245,736

(22) Filed: Feb. 8, 1999

(51) Int. Cl.[7] .............................. C12N 9/00; C12N 1/14; C12N 1/16; C12N 5/04; C12N 5/06
(52) U.S. Cl. .................................... 435/188.5; 435/254.1; 435/255.1; 435/345; 435/410
(58) Field of Search .................. 435/188.5, 254.1, 435/255.1, 410, 745

(56) References Cited

U.S. PATENT DOCUMENTS 5,512,466 * 4/1996 Klee et al. .................... 435/172.3

OTHER PUBLICATIONS

Zhou, G.W., et al. (1994) Science 265, 1059–1064.*

* cited by examiner

Primary Examiner—Charles L. Patterson, Jr.
(74) Attorney, Agent, or Firm—Mark M. Friedman (57) ABSTRACT

Hapten and antigen designed for eliciting catalytic antibodies effective in inhibiting the ethylene production pathway in plants by deactivating a precursor thereof either by decomposition or derivatization. Catalytic antibodies effective in inhibiting the ethylene production pathway in plants by deactivating a precursor thereof. Genes encoding for such catalytic antibodies and plants and cells expressing these genes and producing the catalytic antibodies for controlling the ripening of fruits and vegetables, as well as for controlling senescence of plant tissue.

8 Claims, 2 Drawing Sheets

Fig. 1

S-Adenosyl-
methionine
(SAM)

1-Aminocyclopropane-
1-carboxylic acid
(ACC)

CONTROL OF FRUIT RIPENING AND SENESCENCE IN PLANTS

FIELD AND BACKGROUND OF THE INVENTION

This present invention relates in general to plant molecular biology and more particularly to a method for controlling the ripening of fruit and vegetables as well as controlling the effects of senescence in plants and recombinant DNA molecules capable of affecting the desired control.

The following background information has been reproduced from U.S. Pat. No. 5,512,466.

One of the major problems facing the fruit, vegetable and cut flower industry is the loss of a considerable amount of goods due to spoilage. It is estimated that 12 to 20 percent of the fruit and vegetable products become spoiled from the time they leave the farm until they get to the retail or processing outlets. In the cut flower industry, senescence (the wilting or dying) of the flower before it can be effectively marketed is a significant problem. The spoiling or senescence process observed in fruits, vegetables and cut flowers results in a number of undesirable problems. Chief among these problems is the short harvesting season for the goods and the short shelf life of the goods following the harvest. Furthermore, these spoilage losses ultimately result in a higher cost of the goods to the consumer.

A primary cause of the spoilage of fruits and vegetables is the natural ripening process of the fruit or vegetable. As the fruit or vegetable becomes more ripe it becomes softer and more easily bruised and susceptible to disease or other spoilage causing agents. It is known that ethylene production in the plant stimulates the fruit ripening process and is the key component in the ripening of fruits and vegetables. Ethylene also accelerates flower and leaf senescence. Senescence of flowers treated with the ethylene antagonist STS (silver thiosulfate) was markedly delayed (reviewed in Plant Physiology ed. Tasz, Zeigen 1998) and in Wang and Woodson 1989 Plant Physiology 89: 434–438. Others have attempted to control the ripening of fruits and vegetables in an attempt to extend the shelf life and/or harvesting season of the goods. Many of these attempts have been topical applications of chemicals to the fruit or vegetable itself. These chemical solutions have involved direct applications to the plant in the field or post-harvest applications to the fruit or vegetable itself. Several of these methods are discussed in U.S. Pat. No. 4,957,757 or U.S. Pat. No. 4,851,035. Due to the increasing importance of reducing additional stresses on the environment, a non-chemical means for controlling ripening would be advantageous and beneficial to the industry.

More recently, researchers have used a molecular biology approach to block ethylene synthesis in plants in an attempt to control the ripening of tomatoes. This approach involved transforming a tomato plant with an antisense gene that inhibited the synthesis of ethylene. The antisense gene produces (−) strand RNA that lowers the steady state levels of the (+) strand mRNA encoding a polypeptide involved in the conversion of 1-aminocyclopropane-1-carboxylic acid (ACC) to ethylene by the ethylene forming enzyme ACC oxidase (Hamilton, A., Lycett, G. and Grierson, D. (1990). Antisense gene that inhibits synthesis of the hormone ethylene in transgenic plants. Nature 346:284–287). While this method exhibits some degree of utility, it would be neither easy nor efficient to apply this technology to other plants, because the antisense gene would probably be species and gene specific which would entail obtaining a different antisense gene for each species of plant desired to be transformed.

Similarly, shutting down of ACC synthase, which is the key enzyme of ethylene biosynthesis that catalyses the production of the immediate precursor of ethylene, ACC from S-adenosyl methionine, by using antisense transcript to inactivates the "sense transcript" caused a significant reduction in ethylene biosynthesis and inhibition of fruit ripening (Oeller et al (1991) Science 254: 437–439; Picton et al. Plant J. 3: 469–481 1993).

A more universal method for controlling the ripening of fruits and vegetables as well as a method for controlling senescence of plant tissue is disclosed in U.S. Pat. No. 5,512,466. The method generally embraces the expression of an ACC metabolizing enzyme in the fruit or other desired plant tissue to inhibit the production of ethylene in the fruit or plant tissue. The use of the ACC metabolizing enzyme ACC deaminase is described in detail. The ripening or senescence process in the fruit or plant tissue is inhibited by the expression of the ACC deaminase gene such that the shelf-life and marketability of the fruit or plant is enhanced. The ACC metabolizing enzyme may be used in combination with other methods for reducing ethylene production in transformed plants to further reduce the production of ethylene in the fruit or plant. DNA constructs containing the ACC deaminase gene are also described.

Yet another, novel, more efficient and more universal approach for controlling the ripening of fruits and vegetables, as well as for controlling senescence of plant tissue, would be the expression of a catalytic antibody capable of metabolizing a precursor participating in the synthetic pathway of ethylene in the fruit or other desired plant tissue to inhibit the production of ethylene in the fruit or plant tissue.

There is thus a widely recognized need for, and it would be highly advantageous to have, a catalytic antibody capable of metabolizing a precursor participating in the synthetic pathway of ethylene and genetically modified plants expressing same for controlling the ripening of fruits and vegetables, as well as for controlling senescence of plant tissue.

SUMMARY OF THE INVENTION

According to one aspect of the present invention there is provided a catalytic antibody that is capable of catalyzing the deactivation of a precursor in the synthetic pathway of ethylene in plants, so as to deplete the precursor from the metabolic pool, the catalytic antibody comprising an immunoglobulin that binds a stable transition state analog of a deactivation reaction of the precursor.

According to another aspect of the present invention there is provided a synthetic hapten used to generate antibodies capable of catalyzing the deactivation of a precursor in the synthetic pathway of ethylene in plants comprising a stable transition state analog of a deactivation reaction of the precursor.

According to yet another aspect of the present invention there is provided a synthetic antigen used to generate antibodies capable of catalyzing the deactivation of a precursor in the synthetic pathway of ethylene in plants, comprising a synthetic hapten including a stable transition state analog of the deactivation of the precursor.

According to still another aspect of the present invention there is provided a component part of an antibody which is capable of catalyzing the deactivation of a precursor in the synthetic pathway of ethylene in plants, the component part is selected from the group consisting of an F(ab')2 fragment, an Fab fragment, an Fv fragment, a heavy chain, a light chain, an unassociated mixture of a heavy chain and a light chain, a heterodimer consisting of a heavy chain and a light chain, a catalytic domain of a heavy chain, a catalytic domain of a light chain, a variable fragment of a light chain, a variable fragment of a heavy chain, and a single chain variant of the antibody.

According to an additional aspect of the present invention there is provided a method of generating a catalytic antibody capable of catalyzing the deactivation of a precursor in the synthetic pathway of ethylene in plants comprising the steps of (a) synthesizing a hapten which is a stable transition state analog of a deactivation reaction of precursor in the synthetic pathway of ethylene in plants; and (b) eliciting antibodies to an antigen comprising the hapten.

According to yet additional aspect of the present invention there is provided a method of generating a monoclonal antibody capable of catalyzing the deactivation of a precursor in the synthetic pathway of ethylene in plants comprising the steps of (a) synthesizing a hapten which is a stable transition state analog of the deactivation of the precursor in the synthetic pathway of ethylene in plants; (b) immunizing an animal with an antigen comprising the hapten; (c) isolating immunocytes from the immunized animal; (d) immortalizing the immunocytes; (e) selecting cells secreting the catalytic antibody; and (f) cloning and propagating a line of cells secreting the catalytic antibody.

According to still additional aspect of the present invention there is provided a recombinant, double-stranded DNA molecule which functions in plants to delay ripening of fruit or senescence of plant tissue by causing a reduction of ethylene biosynthesis, the molecule comprising in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence.

Further according to the present invention there is provided a method for producing plants which exhibit a delayed-ripening or senescence of plant tissue phenotype comprising the steps of (a) obtaining regenerable cells of the plant; (b) transforming the cells by inserting into the genome of the cells a recombinant, double-stranded DNA molecule which causes a reduction of ethylene biosynthesis, the molecule comprising in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence; (c) regenerating a plant from the transformed plant cell; and (d) growing the transformed plant to produce fruits which demonstrate delayed ripening.

Still further according to the present invention there is provided a genetically modified plant of fruit which exhibits a delayed-ripening or senescence of plant tissue phenotype, the plant comprising a recombinant, double-stranded DNA molecule which causes a reduction of ethylene biosynthesis, the molecule comprising in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence.

According to further features in preferred embodiments of the invention described below, the precursor is selected from the group consisting of 1-aminocyclopropane-1-carboxylic acid and S-adenosyl methionine.

According to still further features in the described preferred embodiments the precursor is 1-aminocyclopropane-1-carboxylic acid and the stable transition state analog or the hapten is selected from the group consisting of:

wherein X is selected from the group consisting of N atom or P atom;
n is an integer selected from 1–5;
m is an integer selected from 1–3; and
R is selected from the group consisting of an alkyl group and O—.

A specific example is provided by:

According to still further features in the described preferred embodiments the deactivation is decomposition.

According to still further features in the described preferred embodiments the decomposition is hydrolysis, say heterolysis, of a carbon—carbon bond.

According to still further features in the described preferred embodiments the stable transition state analog is covalently bound to a carrier molecule.

The present invention is further of a recombinant nucleic acid molecule comprising a nucleic acid sequence coding for an antibody as described above, a recombinant nucleic acid molecule comprising a nucleic acid sequence coding for a component part of an antibody as described above, a recombinant nucleic acid molecule, wherein transcription of the antibody coding sequence is under a control of a transcriptional promoter effective in a suitable host cell, a recombinant nucleic acid molecule as herein described, further comprising a nucleic acid sequence encoding an in frame signal peptide suitable to promote secretion of the translated antibody. The recombinant nucleic acid molecule according to the present invention preferably further comprises a selection marker suitable for selecting host cells expressing the marker. It can be a deoxyribonucleic acid molecule or a ribonucleic acid molecule in the forms of, where applicable, for example, a naked nucleic acid molecule, a phage vector, a plasmid vector, a cosmid vector, a shuttle vector, a viral vector and a yeast artificial chromosome.

The host cell producing the antibody can be a eukaryotic host cell and a prokaryotic host cell. The eukaryotic host cell can be an animal cell, a plant cell, a fungal cell or a yeast cell. Preferably, the eukaryotic host cell is a plant cell.

Further according to the present invention there are provided recombinant cells or plants transfected with the recombinant nucleic acid described herein; recombinant cells or plants expressing the recombinant nucleic acid described herein; recombinant cells or plants expressing the recombinant nucleic acid described herein; recombinant cells or plants producing a catalytic antibody as described herein; and recombinant cells or plants producing a component part of a catalytic antibody as described herein.

Further according to the present invention there are provided immunocytes immortalized immunocytes producing a catalytic antibody as described herein.

The present invention successfully addresses the shortcomings of the presently known configurations by providing a novel and universal way to inhibit ethylene production in fruits and plant tissue, to thereby control or delay ripening of fruits and vegetables, as well as for controlling senescence of plant tissue.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of haptens and antigens designed for eliciting catalytic antibodies effective in inhibiting the ethylene production pathway in plants by deactivating a precursor thereof. The present invention is further of catalytic antibodies effective in inhibiting the ethylene production pathway in plants by deactivating a precursor thereof. The present invention is further of genes encoding for such catalytic antibodies and of plants and cells expressing these genes and producing the catalytic antibodies. The present invention can therefore be used for controlling the ripening of fruits and vegetables, as well as for controlling senescence of plant tissue.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 1:
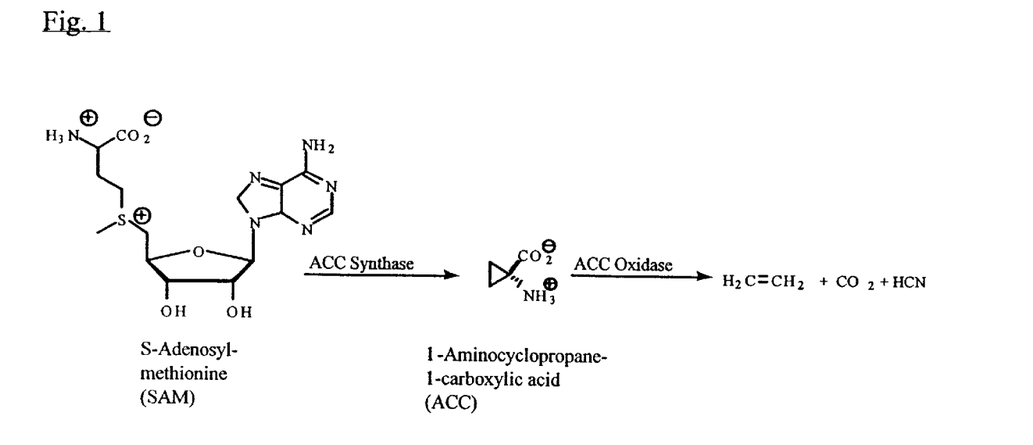
FIG. 1 is a description of a part of the ethylene synthetic pathway in plants.

The metabolic pathway for the production of ethylene in plants is as follows (see also FIG. 1):

The amino acid methionine is the precursor of ethylene. To inhibit the production of ethylene in plants, one possible method would be to metabolize one or more of its precursors 1-aminocyclopropane-1-carboxylic acid (ACC) or S-adenosyl methionine (SAM) and remove it from the metabolic pool (FIG. 1). However, since the rate-limiting step in the pathway is the conversion of S-adenosyl-methionine to ACC, which is catalyzed by the enzyme ACC synthase, preferably ACC is metabolized. The conversion of ACC to ethylene, requires oxygen and is catalyzed by the enzyme ACC oxidase (Plant Physiology, $2^{nd}$ edition, Eds. Taiz and Zeiger, Sinauer Associates, Inc., Publishers, 1998).

An approach is disclosed herein that makes use of genetically modified plants producing catalytic antibodies effective in metabolizing a precursor in the synthesis of ethylene, such as ACC or S-adenosyl methionine.

As used herein in the specification and in the claims section below, the term "genetically modified" includes the terms transgenic and genetically transformed.

In principle, catalytic antibodies are elicited against stable analogs of postulated transition states of highest energy of the reaction to be catalyzed. The transition state structure itself cannot be characterized experimentally due to its very short lifetime.

Figure 2:
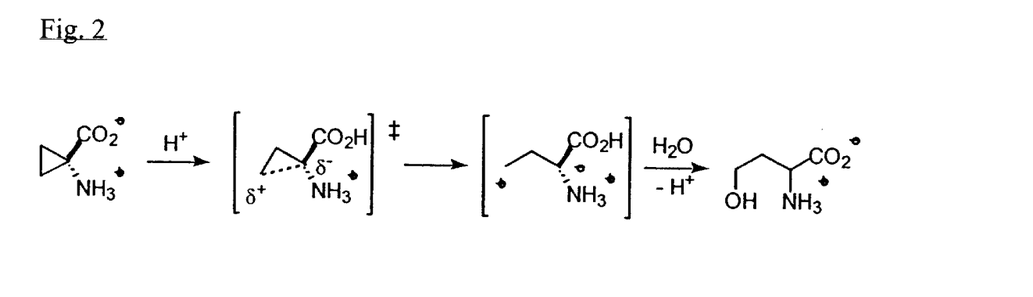
FIG. 2 is a description of an antibody catalyzed decomposition of ACC according to the present invention, wherein transition states are in brackets.
Figure 4:
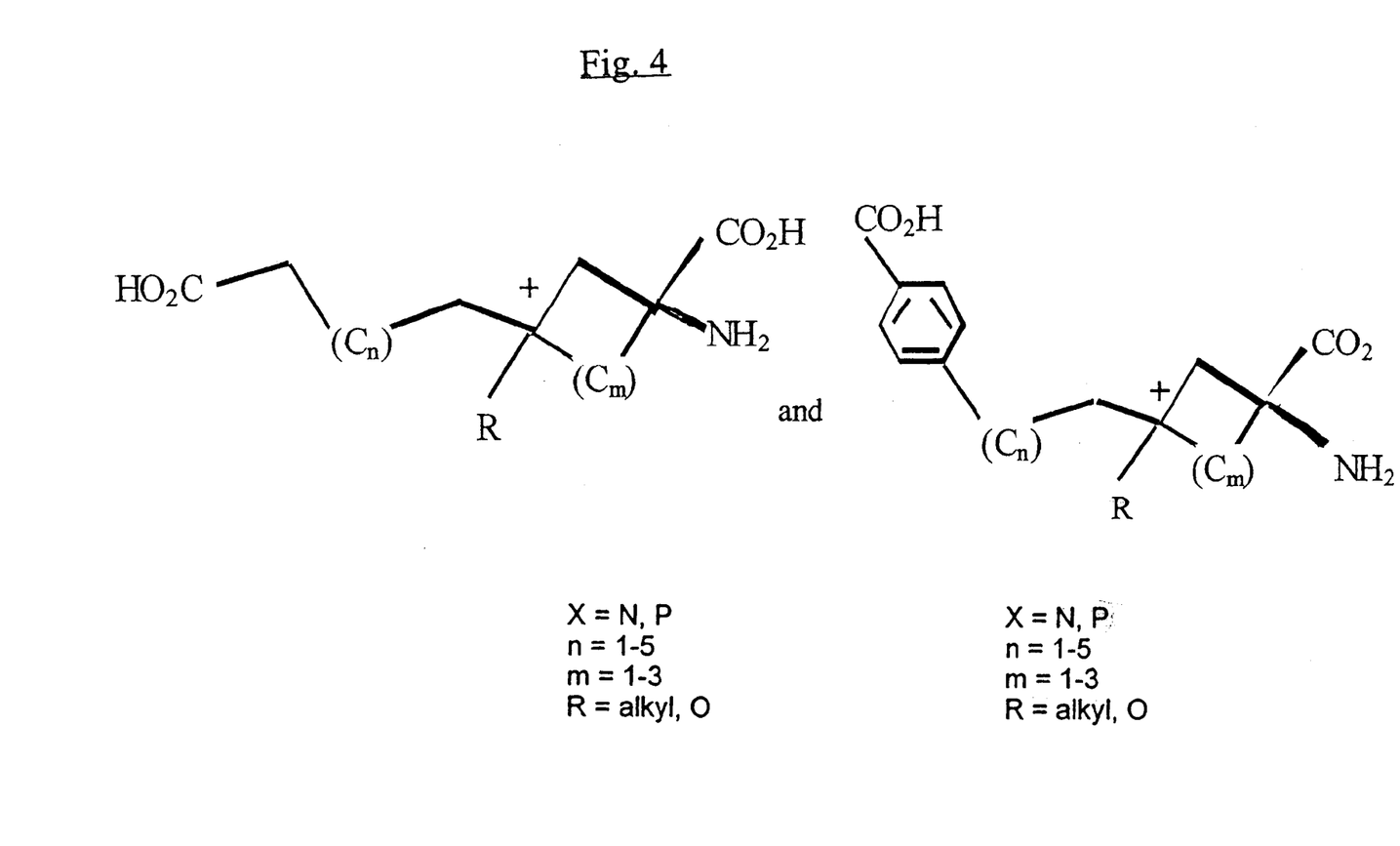
FIG. 4 provides exemplary stable transition state analogs according to the present invention.

A mechanism for the catalyzed decomposition of ACC is proposed herein and is shown in FIG. 2. To cleave the carbon—carbon bond in the cyclopropane ring it is suggested to stabilize a negative charge on the carbon $\alpha$ to the carboxyl group and also stabilize a positive charge on the carbon $\beta$ to the carboxyl group. Several transition state analogs which can be used as haptens for eliciting catalytic antibodies for decomposing ACC are described in FIG. 4.

Figure 3:
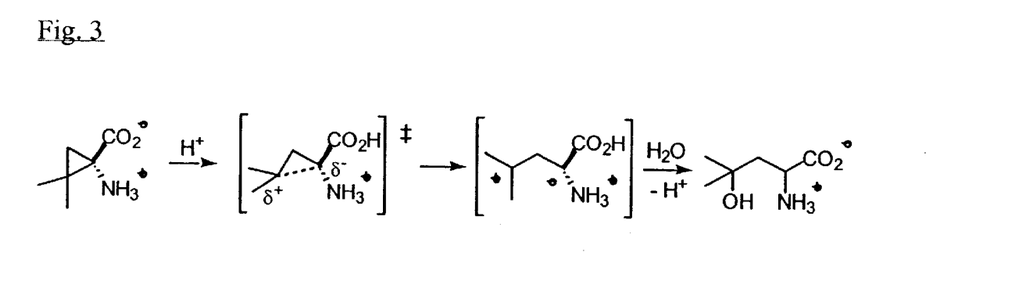
FIG. 3 is a description of acid catalyzed decomposition of 2,2-dimethyl ACC according to prior art studies, wherein transition states are in brackets.

This cleavage mode of ACC described in FIG. 2 is based on prior art of acid-catalyzed cleavage of 2,2-dimethyl-ACC (De Kimpe, N.; Sulman, P.; Brunet, P.; Lambein, F.; Schamp, N. Tetrahedron Lett. 1989, 30, 1863). It has been reported by Kimpe et al. that 2,2-dimethyl-ACC is readily hydrolyzed under acidic conditions to produce a γ-hydroxy-amino acid, as specifically shown in FIG. 3. This is not surprising, because the C—C bond cleavage in FIG. 3 involves the formation of a stable tertiary carbocation intermediate. Although the analogous reaction of FIG. 2 involves a primary rather than a tertiary carbocation intermediate, there is prior art in the field of catalytic antibodies where an antibody was shown to efficiently catalyze a reaction that involves a primary carbocation (Li, T.; Janda, K. D.; Ashley, J. A.; Lerner, R. A. Science 1994, 264, 1289.). The overall transformations that were catalyzed by that specific antibody included various cationic cyclization reactions. Certainly, it is more difficult to carry out such cyclization reactions than a simple hydrolytic cleavage reaction illustrated in FIG. 2. Moreover, it has been demonstrated by prior art that a number of hydrolytic reactions, including hydrolysis of ketals and acetals, epoxides and enol ethers, were efficiently catalyzed by catalytic antibodies which were elicited against quaternary ammonium haptens. For further details the reader if referred to Shabat, D.; Shulman, H.; Itzhaky, H.; Reymond, J. -L.; Keinan, E. Chem. Commun. 1998, 16, 1759. Sinha, S. C.; Keinan, E. Isr. J. Chem. 1996, 36, 185. Sinha, S. C.; Keinan, E. J. Am. Chem. Soc. 1995, 117, 3653. Jahangiri, G. K.; Reymond, J. -L. J. Am. Chem. Soc. 1994, 116, 11264. Reymond, J. -L.; Jahangiri, G. K.; Stoudt, C.; Lerner, R. A. J. Am. Chem. Soc. 1993, 115, 3909. Reymond, J. -L.; Reber, J. -L.; Lerner, R. A. Angew. Chem. 1994, 106, 485. Sinha, S. C.; Keinan, E.; Reymond, J. -L. Proc. Natl. Acad. Sci. U. S. A. 1993, 90, 11910. Shabat, D.; Itzaky, H.; Reymond, J. -L.; Keinan, E.; Nature 1995, 374, 143. Shabat, D.; Sinha, S. C.; Reymond, J. -L.; Keinan, E. Angew. Chem. 1996, 35, 2628. Sinha, S. C.; Keinan, E.; Reymond, J. -L. J. Am. Chem. Soc. 1993, 115, 4893. Reymond, J. -L.; Janda, K. D.; Lerner, R. A. Angew. Chem. Int. Ed. Engl. 1991, 30, 1711. Reymond, J. -L.; Lerner, R. A. J. Am. Chem. Soc. 1992, 114, 2257. Sinha, S. C.; Keinan, E.; Reymond. J. -L. J. Am. Chem. Soc. 1993, 115, 4893.

The position of a positively charged tetrahedral nitrogen in the azetidine ring is designed to elicit complementary negative charges in the antibody active site. Such negatively charged groups, when appropriately positioned with respect to ACC, will stabilize the developing positive charge in the transition state of the reaction and therefore catalyze the carbon—carbon bond cleavage under neutral conditions. The 4-member azetidine ring is chosen for its resemblance to the inflated cyclopropane ring during the carbon—carbon bond elongation. As described above, quaternary ammonium salts have already been used as transition state analogs in the past for eliciting charged active sites in highly efficient hydrolytic catalytic antibodies. Such antibodies, in particular antibody 14D9, have exhibited high efficiency in catalyzing a broad variety of organic reactions, in which there is accumulation of positive charge in the transition state. These reactions include the hydrolysis of ketals, epoxides, enol ethers and ketalization reaction (Reymond, J. -L.; Jahangiri, G. K.; Stoudt, C.; Lerner, R. A. J. Am. Chem. Soc. 1993, 115, 3909. Reymond, J. -L.; Reber, J. -L.; Lerner, R. A. Angew. Chem. 1994, 106, 485. Sinha, S. C.; Keinan, E.; Reymond, J. -L. Proc. Natl. Acad. Sci. U. S. A. 1993, 90, 11910).

A significant aspect of the present invention is to provide a mechanism for delaying the ripening of fruit or senescence in plants by reducing the steady state levels of ACC in the plant tissues which reduces the level of ethylene in the plant tissues. It is preferred that the steady state concentrations of ethylene or ACC in the plant be reduced by at least about 70% from normal levels in a non-modified cultivar.

Preferably, the ethylene or ACC concentrations are reduced by at least about 90% from normal levels. It is believed that the reduction of the steady state levels of ACC or ethylene in a plant or the fruit of a plant can be achieved by various methods, all of which are considered within the scope of the instant invention.

Regarding the delaying of ripening of fruit, it is preferred that the fruit be delayed from ripening on the vine by 1 to 30 days. This delay is to be measured from the onset of ripening and, specifically with respect to tomato, from when the fruit reaches the breaker stage of ripening.

Likewise, the fruit is preferably delayed in ripening from 1 to 90 days following detachment from the vine and more preferably between 5 and 30 days. With respect to tomato, this delay in ripening is measured from the time of detachment of the fruit from the vine when the fruit is removed at the mature green or breaker stage of ripening. It is to be understood that the delay in ripening after detachment from the vine can be extended beyond the terms described by cold storage or other methods known in the art.

Thus, the present invention relates to antigens which are capable of eliciting through immunogenic methods antibodies which can catalyze the deactivation of a precursor in the ethylene production pathway either by decomposition or by derivatization. These antigens comprise a hapten, or a hapten linked to a suitable carrier molecule, wherein the hapten is chosen, inter alia, because it resembles a presumed transition state structure of the precursor deactivation reaction, and is therefore defined herein and in the claims as a "transition state analog". A compound is defined as a "stable" analog if it is robust enough to withstand isolation in useful quantities. The antibodies elicited are capable of catalyzing a chemical reaction, and are therefore defined herein and in the claims as "catalytic antibodies". The catalytic antibodies according to the present invention are designed to inactivate the precursor by binding the presumed transition state structure in a rate limiting step of the deactivation reaction of the precursor.

The terms "decomposition" and "degradation" are interchangeably used herein to indicate hydrolysis of the precursor. The term "derivatization" and the above terms both result in "deactivation" or "depletion" of the precursor from the metabolic pathway. These terms are used herein to indicate a chemical reaction whereby the precursor is prevented from the ethylene pathway either by being decomposed or degraded, i.e., hydrolyzed, or by being derivatized and, in both cases, not accessible to the enzymes participating in the ethylene pathway.

Catalysts increase chemical reaction rates by lowering the activation energy of a reaction. Antibodies elicited to a hapten or immunogen according to the invention, should stabilize the energy of the transition state relative to the reactants and products. This approach has been successfully demonstrated in the generation of specific catalytic monoclonal antibodies. Catalytic antibodies elicited with haptens according to the invention are "specific" in that they are designed to catalyze only the cleavage of certain chemical bonds having the selected structural elements or conformations.

Catalytic antibodies may be obtained by processes comprising generating a plurality of monoclonal antibodies to an antigen and screening the plurality of antibodies so generated to identify a monoclonal antibody that catalyzes the reaction of interest. Antibodies may be generated either in vitro or in vivo.

In still a further and related process, an animal is immunized with an antigen thereby generating antibody producing lymphocytes in said animal, antibody producing lymphocytes are removed from the animal, said lymphocytes are fused with myeloma cells to produce a plurality of hybridoma cells, each of which produces monoclonal antibodies, the plurality of monoclonal antibodies is screened to identify a monoclonal antibody that catalyzes the reaction, and the hybridoma producing the catalytic antibody is cloned.

As used herein and in the claims, the term "animal" refers to any organism with an immune system.

As used herein and in the claims, the terms antibody or immunoglobulin, which are interchangeably used herein, refer to any of several classes of structurally related proteins that function as part of the immune response of an animal, which proteins include IgG, IgD, IgE, IgA, IgM and related proteins. These terms further relate to chimeric immunoglobulins which are the expression products of fused genes derived from different species. These terms further relate to immunologically active derivatives of the above proteins, as further detailed hereinunder.

Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains.

Known active fragments of catalytic immunoglobulin molecules will include the $F(ab')_2$ portion, Fab fragments and Fv fragments.

In still a further related process in vitro grown cells are immunized with an antigen thereby generating antibody producing lymphocytes in vitro, said lymphocytes are fused with myeloma cells to produce a plurality of hybridoma cells each of which produces monoclonal antibodies, the plurality of monoclonal antibodies is screened to identify a monoclonal antibody that catalyzes the reaction, and the hybridoma producing the catalytic antibody is cloned.

In still further related processes nucleic acids encoding the catalytic antibodies, or active fragments thereof, are isolated and cloned. These nucleic acids may be used to create cells which produce in vivo catalytic antibodies. Cells may be taken from an organism and genetically engineered to produce the catalytic antibodies or fragments thereof. The protein may be designed by known methods to remain within the cell, to remain on the cell surface or to be secreted from the cell.

In still further related processes the cloned nucleic acids are introduced into plant cells, via a suitable vector, enabling production of the antibodies in plants, thereby depleting the precursor from the metabolic pool and substantially inhibiting the production of ethylene. As a result, such plants will show regression in ripening of fruits and vegetables, as well as in senescence of plant tissue.

Selection and Synthesis of Antigens:

According to the present invention an antigen is selected from the group consisting of (i) a hapten comprising a stable transition state analog of the desired chemical reaction; or (ii) the hapten linked to a carrier molecule.

According to the present invention the hapten will be an analog of the transition state structure in a deactivation reaction of the precursor. Details concerning the structure, transition states, and a stable transition state analog of an ACC decomposition reaction are provided hereinabove in relation to FIGS. 2–4.

Transition state analogs are designed to mimic one of the presumed transition structures of the reaction to be catalyzed. Examples of such transition state analogs are well known in the art, and have been reviewed extensively (see for example Lerner et al. Science 252, 659–667, 1991).

Generation of Monoclonal Catalytic Antibodies:

Methods for the generation and selection of monoclonal antibodies are well known in the art, as summarized, for example, in reviews such as Tramontano and Schloeder, Methods in Enzymology 178, 551–568, 1989.

The haptens of the present invention may be used to generate antibodies in vitro. More preferably, the haptens will be used to elicit antibodies in vivo, by coupling the hapten to a suitable carrier to produce an immunogen.

In general, a suitable host animal is immunized with the immunogen of choice. Advantageously, the animal host used will be a mouse of an inbred strain.

According to a preferred embodiment of the present invention the animal(s) will be immunized with an immunogen which comprises one or more molecules of the hapten of interest covalently linked to a suitable carrier. The carrier of choice may be selected from the group consisting of proteins, natural or synthetic peptides or polypeptides, or any other suitable carrier moiety. Well known examples of such carriers include, but are not limited to, proteins such as bovine serum albumin, human serum albumin, keyhole limpet hemocyanin, linear or branched copolymers of amino acids, and the like.

Animals are typically immunized with a mixture comprising a solution of the immunogen in a physiologically acceptable vehicle, and any suitable adjuvant, which achieves an enhanced immune response to the immunogen. By way of example, the primary immunization conveniently may be accomplished with a mixture of a solution of the immunogen and Freund's complete adjuvant, said mixture being prepared in the form of a water in oil emulsion. Typically the immunization may be administered to the animals intramuscularly, intradermally, subcutaneously, intraperitoneally, into the footpads, or by any appropriate route of administration.

The immunization schedule of the immunogen may be adapted as required, but customarily involves several subsequent or secondary immunizations using a milder adjuvant such as Freund's incomplete adjuvant.

Antibody titers and specificity of binding to the hapten can be determined during the immunization schedule by any convenient method including, by way of example, radioimmunoassay, or enzyme linked immunoassay.

Antibody activity assays can be based on detection of the reaction product of the catalytic deactivation of the precursor, assays based on the disappearance of the intact precursor, and in terms of catalytic efficiency in the desired deactivation reaction such as hydrolysis of the precursor.

Antibody activity assays based on the detection of reaction products or on the disappearance of substrate may conveniently be followed by spectrophotometric means, by high pressure liquid chromatography (HPLC) or by means of any other suitable detection system.

When suitable antibody titers are achieved, antibody producing lymphocytes from the immunized animals are obtained, and these are cultured, selected and cloned, as is known in the art.

Typically, lymphocytes may be obtained in large numbers from the spleens of immunized animals, but they may also be retrieved from the circulation, the lymph nodes or other lymphoid organs.

Lymphocytes are then fused with any suitable myeloma cell line, to yield hybridomas, as is well known in the art.

Alternatively, lymphocytes may also be stimulated to grow in culture, and may be immortalized by methods known in the art including the exposure of these lymphocytes to a virus, a chemical or a nucleic acid such as an oncogene, according to established protocols.

After fusion, the hybridomas are cultured under suitable culture conditions, for example in multiwell plates, and the culture supernatants are screened to identify cultures containing antibodies that recognize the hapten of choice.

Hybridomas that secrete antibodies that recognize the hapten of choice are cloned by limiting dilution and expanded, under appropriate culture conditions. Monoclonal antibodies are purified and characterized in terms of immunoglobulin type, binding affinity and in terms of efficiency of catalysis of the hydrolysis reaction of the mycotoxin.

Cloning of Nucleic Acids for Catalytic Antibodies:

Cloning of cDNA encoding catalytic antibodies or fragments thereof may be accomplished by several approaches known in the art. In the preferred approach, mRNA from clonal hybridoma cell lines which produce catalytic antibodies is employed as starting material. The cells are harvested and mRNA is extracted by standard methods known in the art. The cDNA is prepared by reverse transcription of the mRNA by standard methods known in the art. The cDNA for each chain of the immunoglobulin is cloned separately, and may be amplified by polymerase chain reaction using appropriate primers. The cDNA is then ligated into appropriate vectors by standard methods. The cDNA may be cloned into expression vectors and expressed separately in any convenient expression system, so that the properties of the expressed single chains of the antibodies may be determined. Alternatively, the individual chains may be expressed in the same cells which are then screened for the production of recombinant active antibodies.

The method of using the invention will be modified in accordance with the system that is selected according to the current principles that are known in the art of recombinant protein production.

According to the present invention the genetic information for the production of the catalytic antibody of interest is introduced into the host plant cells by an appropriate plant cell vector as is known in the art. The present invention provides information that will enable the skilled artisan to prepare constructs of genetic material comprising an open reading frame that encodes at least one chain of a novel catalytic antibody capable of inactivating the precursor of choice.

The most commonly used method for DNA mediated transformation of plants is to employ *Agrobacterium tumefaciens* as the delivery vehicle for introduction of recombinant vectors to the plant cell nucleus (Bevan and Chilton, Ann. Rev. Genetics 16, 357–384, 1982).

Plant expression vectors are generally large and contain only one promoter and one polylinker region, and therefore it is useful to express only one immunoglobulin in each vector and to transform plants separately with individual heavy and light chain expressing vectors.

Plants producing functional antibodies are produced in the progeny of a cross pollination between the individual heavy of light chain containing plants.

In certain embodiments it will suffice to produce an active fragment of the catalytic activity, for instance a Fab fragment of the intact antibody or even an Fv fragment thereof.

In addition to the nucleic acid encoding the protein or polypeptide of choice, the constructs of the invention may comprise the following elements: a selectable marker, an origin of replication, a transcriptional promoter, a translation start site, a signal sequence for secretion of the product.

In one aspect, the novelty of the invention resides in the DNA which encodes at least part of one chain of the catalytic antibody that depletes the precursor, optionally in any combination with the elements recited above.

The present disclosure also teaches various means to exploit the commercial potential of these catalytic antibodies by inhibiting ripening of fruits and vegetables, as well as inhibiting senescence of plant tissue.

Vector of choice: Once a gene encoding a portion of a catalytic antibody has been identified and isolated, it must be engineered for plant expression. To introduce such a gene into a plant, a suitable chimeric gene and transformation vector must be constructed. A typical chimeric gene for transformation into a plant will include a promoter region, a heterologous structural DNA coding sequence and a 3' non-translated polyadenylation site. A heterologous structural DNA coding sequence means a structural coding sequence that is not native to the plant being transformed. Heterologous with respect to the promoter means that the coding sequence does not exist in nature in the same gene with the promoter to which it is now attached. Chimeric means a novel non-naturally occurring gene which is comprised of parts of different genes. In preparing the transformation vector, the various DNA fragments may be manipulated as necessary to create the desired vector. This includes using linkers or adaptors as necessary to form suitable restriction sites or to eliminate unwanted restriction sites or other like manipulations which are known to those of ordinary skill in the art.

Promoters which are known or found to cause transcription of selected gene or genes in plant cells can be used in the present invention. Such promoters may be obtained from plants, plant pathogenic bacteria or plant viruses and include, but are not necessarily limited to, the 35S and 19S promoters of cauliflower mosaic virus (CaMV35S and CaMV19S), the full-length transcript promoter from the figwort mosaic virus (FMV35S) and promoters isolated from plant genes such as EPSP synthase, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of the catalytic antibody to substantially inhibit the production of ethylene. Those skilled in the art will recognize that the amount of the antibody needed to inhibit ethylene production may vary with the type of plant and the tissues within the plant of interest.

Particularly useful promoters for use in the present invention are fruit specific promoters which are expressed during ethylene production in the fruit and the full-length transcript promoter from the figwort mosaic virus (FMV35S). The FMV35S promoter is particularly useful because of its ability to cause uniform and high levels of expression of the antibody in plant tissues. The DNA sequence of a FMV35S promoter is presented in U.S. Pat. No. 5,512,466 and is identified as SEQ ID NO: 17 therein. Examples of fruit specific promoters include the E8, E4, E17 and J49 promoters from tomato (Lincoln, J. and Fischer, R. (1988). Diverse mechanisms for the regulation of ethylene-inducible gene expression. Mol Gen Genet 212, 71–75), as well as the 2A11 promoter as described in U.S. Pat. No. 4,943,674.

The promoters used for expressing the antibody encoding gene or genes of this invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" or "FMV35S" promoter includes variations of these promoters, e.g., promoters derived by means of ligation with operator regions, random or controlled mutagenesis, addition or duplication of enhancer sequences, etc.

The 3' non-translated region contains a polyadenylation signal which functions in plants to cause the addition of polyadenylated nucleotides to the 3' end of the RNA sequence. Examples of suitable 3' regions are the 3' transcribed, non-translated regions containing the polyadenylation signal of the tumor-inducing (Ti) plasmid genes of Agrobacterium, such as the nopaline synthase (NOS) gene, and plant genes like the 7s soybean storage protein genes and the pea E9 small subunit of the RuBP carboxylase gene (ssRUBISCO).

The RNA produced by a DNA construct of the present invention also preferably contains a 5' non-translated leader sequence. This sequence can be derived from the promoter selected to express the gene or genes, and can be specifically modified so as to increase translation of the mRNAs. The 5' non-translated regions can also be obtained from viral RNA's, from suitable eukaryotic genes, or from a synthetic gene sequence. The present invention is not limited to constructs wherein the non-translated region is derived from the 5' non-translated sequence that accompanies the promoter sequence. Rather, the non-translated leader sequences can be part of the 5' end of the non-translated region of the native coding sequence for the heterologous coding sequence, or part of the promoter sequence, or can be derived from an unrelated promoter or coding sequence as discussed above.

In order to construct vectors capable of directing expression the catalytic antibodies according to the present invention specifically to fruit, a tomato fruit specific transcriptional promoter needs to be used. The promoter that was chosen is known to be induced to express at high levels in the presence of ethylene and is also known to be limited to the tomato fruit (Lincoln, J. and Fischer, R. (1988). Diverse mechanisms for the regulation of ethylene-inducible gene expression. Mol Gen Genet 212, 71–75). The DNA sequence of the promoter for this gene, E8, has been published (Deikman, J. and Fischer, R. (1988). Interaction of a DNA binding factor with the 5'-flanking region of an ethylene-responsive fruit ripening gene from tomato. EMBO J. 7, 3315–3320). The DNA sequence of the E8 promoter is designated SEQ ID NO: 10 and is illustrated in FIG. 14 of U.S. Pat. No. 5,512,466, which also provides a detailed protocol for its isolation. While this promoter was chosen, other fruit specific promoters would also be useful and their identification and isolation routine to one of ordinary skill in the art.

In a preferred embodiment according to the present invention, the vector that is used to introduce the encoded protein into the host cells of the plant will comprise an appropriate selectable marker. In a more preferred embodiment according to the present invention the vector is a plant expression vector comprising both a selectable marker and an origin of replication. In another most preferred embodiment according to the present invention the vector will be a shuttle vector, which can propagate both in *E. coli* (wherein the construct comprises an appropriate selectable marker and origin of replication) and be compatible for propagation or integration in the genome of the organism of choice. In yet another embodiment, the construct comprising the promoter of choice, and the gene of interest is placed in a viral vector which is used to infect the cells. This virus may be integrated in the genome of the organism of choice or may remain non-integrated.

While the DNA encoding at least part of one chain of the catalytic antibody is an essential element of the invention, it is modular and can be used in different contexts. The promoter of choice that is used in conjunction with this invention will comprise any suitable promoter as further detailed hereinabove. It will be appreciated by one skilled in the art, however, that it is necessary to make sure that the transcription start site(s) will be located upstream of open reading frame. In a preferred embodiment of the present invention, the promoter that is selected will comprise an element that is active in the particular host plant cells of interest.

These elements may be selected from transcriptional regulators that activate the transcription of genes essential for the survival of these cells in conditions of stress or starvation, including the heat shock proteins. Promoters containing this type of sequence may advantageously be used according to the present invention.

As further detailed hereinabove, DNA sequences encoding the translational start site (ATG) of the gene to be expressed, will be placed downstream of the transcription start site(s). Any equivalent functional element selected from similar elements in this or other organisms may be used as appropriate in the organism of choice. Equivalent functional elements will include elements with synthetic bases, or elements found in other genes of plants as well as elements found in genes of other unicellular or multicellular organisms.

According to one embodiment of the present invention secretion of the protein out of the cell is preferred. In this embodiment the construct will comprise a signal sequence to effect secretion as is known in the art. A signal sequence that is recognized in the active growth phase will be most preferred. As will be recognized by the skilled artisan, the appropriate signal sequence should be placed immediately downstream of the translational start site (ATG), and in frame with the coding sequence of the gene to be expressed.

Introduction of the Construct into the Microorganism or Cell Line of Choice:

Introduction of the construct into the cells is accomplished by any conventional method for transfection, infection or the like as is known in the art. In constructs comprising a selectable marker the cells may be selected for those bearing functional copies of the construct. If the plasmid comprising the gene of interest is episomal the appropriate selective conditions will be used during growth. Stable transfectants and stable cell lines may be derived from the transfected cells in appropriate cases, in order to conveniently maintain the genotype of interest. Cell growth is accomplished in accordance with the cell type, using any standard growth conditions as may be suitable to support the growth of the specific cell line.

Catalytic Antibody Production in Genetically Modified Plant Cells:

The production of monoclonal antibodies in plants may be accomplished by plant transformation and regeneration, as is well known in the art. Alternatively, vectors encoding immunoglobulin heavy and light chains can be introduced into plant cell protoplasts by methods known in the art, such as by means of eletroporation, or by using polyethylene glycol as a facilitator.

Transient expression will result in the synthesis, assembly and optionally secretion of functional antibodies. This system is more rapid than plant transformation and regeneration and may advantageously be used to optimize the parameters of the vector constructs. Thus, this system will be useful to optimize the type and arrangement of promoters.

Analysis of regenerated plants the heavy and light chain constructs have shown that the native signal sequence on the transcript contributes significantly to the accumulation of the heavy or light chains while expression of individual chains was barely detectable in constructs without signal sequences (Haitt et al., Nature 342, 66, 1989).

The characterization of antibodies from plants has previously described antibodies which have been targeted for secretion through the plasma membrane. Alternative techniques for the efficient production of intracellular antibodies might include the single chain antibody construct (Chaudhary et al., Proc. Natl. Acad. Sci. USA 87, 1066–1069, 1990) in which endomembrane associated assembly of heavy and light chains is replaced by refolding of variable regions joined by a peptide linker.

A DNA construct of the present invention can be inserted into the genome of a plant by any suitable method. Suitable plant transformation vectors include those derived from a Ti plasmid of Agrobacterium tumefaciens, such as those disclosed by, Bevan and Chilton, Ann. Rev. Genetics 16, 357–384, 1982; U.S. Pat. No. 4,940,838 and others. In addition to plant transformation vectors derived from the Ti or root-inducing (Ri) plasmids of Agrobacterium, alternative methods can be used to insert the DNA constructs of this invention into plant cells. Such methods may involve, for example, the use of liposomes, electroporation, chemicals that increase free DNA uptake, particle gun technology, and transformation using viruses. Methods for the introduction of vectors into maize, or other monocot cells would include, but are not limited to, the injection method of Neuhaus, G. et al. (1987) Theor. Appl. Genet. 75:30, the injection method of de la Pena, A., Lorz, H. and Schell, J. (1987) Nature 325:274–276 or the microprojectile methods of Klein, T. M., Wold, E. D., Wu, R. and Sanford, J. C. (1987) Nature 327:70–73 and McCabe, D. E., et al. (1988) Bio/Technology 6:923.

The construction of vectors capable of being inserted into a plant genome via Agrobacterium tumefaciens mediated delivery is known to those of ordinary skill in the art. Typical plant cloning vectors comprise selectable and scoreable marker genes, T-DNA borders, cloning sites, appropriate bacterial genes to facilitate identification of transconjugates, broad host-range replication and mobilization functions and other elements as desired.

If Agrobacterium mediated delivery is chosen, once the vector has been introduced into the disarmed Agrobacterium strain, the desired plant can then be transformed. Any known method of transformation that will work with the desired plant can be utilized.

Plant Varieties:

Plants particularly suitable for use in this invention are tomato, banana, kiwi fruit, avocado, melon, mango, papaya, apple, peach, and other climacteric fruit plants. The present invention should also be suitable for use in the following non-climacteric species: strawberry, lettuce, cabbage, cauliflower, onions, broccoli, cotton, canola and oilseed rape.

Other plant species that are affected by the ethylene induced ripening process may also benefit from the teachings of the present invention especially those in which ethylene production is critical to the growth of the plant or the ripening or development of the fruit of the plant. In the cut flower industry, particularly desirable flower species would be carnations, roses and the like. Foliage vegetables are also candidates. This list should be interpreted as only illustrative and not limiting in any sense.

Thus, according to one aspect of the present invention there is provided a catalytic antibody that is capable of catalyzing the deactivation (either decomposition or degradation, or derivatization) of a precursor in the synthetic pathway of ethylene in plants, so as to deplete the precursor from the metabolic pool. The catalytic antibody according to the present invention includes an immunoglobulin that binds a stable transition state analog of a deactivation reaction of the precursor.

According to another aspect of the present invention there is provided a synthetic hapten or antigen used to generate antibodies capable of catalyzing the deactivation (either decomposition or degradation, or derivatization) of a precursor in the synthetic pathway of ethylene in plants. The hapten or antigen according to the present invention comprises a stable transition state analog of a deactivation reaction of the precursor.

According to still another aspect of the present invention there is provided a component part of an antibody which is capable of catalyzing the deactivation (either decomposition or degradation, or derivatization) of a precursor in the synthetic pathway of ethylene in plants. The component part according to the present invention is selected from the group consisting of an F(ab')$_2$ fragment, an Fab fragment, an Fv fragment, a heavy chain, a light chain, an unassociated mixture of a heavy chain and a light chain, a heterodimer consisting of a heavy chain and a light chain, a catalytic domain of a heavy chain, a catalytic domain of a light chain, a variable fragment of a light chain, a variable fragment of a heavy chain, and a single chain variant of the antibody.

According to an additional aspect of the present invention there is provided a method of generating a catalytic antibody capable of catalyzing the deactivation (either decomposition or degradation, or derivatization) of a precursor in the synthetic pathway of ethylene in plants. The method is effected by implementing the following method steps, in which, in a first step, a hapten which is a stable transition state analog of a deactivation reaction of precursor in the synthetic pathway of ethylene in plants is synthesized. Then, antibodies are elicited to an antigen comprising the hapten.

According to yet additional aspect of the present invention there is provided a method of generating a monoclonal antibody capable of catalyzing the deactivation (either decomposition or degradation, or derivatization) of a precursor in the synthetic pathway of ethylene in plants. The method according to this aspect of the present invention is effected by implementing the following method steps, in which, in a first step, a hapten which is a stable transition state analog of the deactivation of the precursor in the synthetic pathway of ethylene in plants is synthesized. Then, an animal is immunized with an antigen comprising the hapten. Thereafter immunocytes are isolated from the immunized animal. Subsequently, the immunocytes are immortalized, Thereafter, cells secreting the catalytic antibody are selected. And, finally a line of cells secreting the catalytic antibody is cloned and propagated.

According to still additional aspect of the present invention there is provided a recombinant, double-stranded DNA molecule which functions in plants to delay ripening of fruit or senescence of plant tissue by causing a reduction of ethylene biosynthesis. The molecule includes in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence.

Further according to the present invention there is provided a method for producing plants which exhibit a delayed-ripening or senescence of plant tissue phenotype. The method is effected by (a) obtaining regenerable cells of the plant; (b) transforming the cells by inserting into the genome of the cells a recombinant, double-stranded DNA molecule which causes a reduction of ethylene biosynthesis, the molecule comprising in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence; (c) regenerating a plant from the transformed plant cell; and (d) growing the transformed plant to produce fruits which demonstrate delayed ripening.

Still further according to the present invention there is provided a genetically modified plant of a fruit which exhibits a delayed-ripening or senescence of plant tissue phenotype. The plant comprising a recombinant, double-stranded DNA molecule which causes a reduction of ethylene biosynthesis, the molecule comprising in sequence in the 5' to 3' direction (i) at least one promoter region (e.g., CaMV35S, FMV35S, 2A11 or E8) which functions in ripening fruit to cause the production of an RNA sequence, the promoter region being operably linked to; (ii) at least one structural DNA sequence that causes the production of at least one RNA sequence that encodes at least one component part of a catalytic antibody, the catalytic antibody being capable of deactivating a precursor in the synthetic pathway of ethylene, the at least one structural sequence being operably-linked to; (iii) at least one 3' non-translated region that functions in plant cells to polyadenylate the 3' end of the at least one RNA sequence; wherein the at least one promoter is heterologous with respect to the structural DNA sequence.

According to a preferred embodiments of the present invention, and as further described and reasoned hereinabove, the precursor of the ethylene synthetic pathway is selected from the group consisting of 1-aminocyclopropane-1-carboxylic acid and S-adenosyl methionine, the former is the presently preferred precursor.

According to another preferred embodiment of the present invention, the precursor is 1-aminocyclopropane-1-carboxylic acid and the stable transition state analog or the hapten is selected from the group consisting of:

wherein X is selected from the group consisting of N atom or P atom;

$C_n$ is an integral number of carbon atoms from 1 to 5;
$C_m$ is an integral number of carbon atoms from 1 to 3;
R is selected from the group consisting of an alkyl group and O—.

A specific example is provided by:

The stable transition state analog or hapten according to the present invention is preferably covalently bound to a carrier molecule.

The decomposition reaction according to the present invention is preferably a hydrolysis reaction. In a preferred embodiment a carbon—carbon bond in the precursor molecule is hydrolyzed (see FIG. 2 an accompanying descriptions hereinabove).

The present invention is further of a recombinant nucleic acid molecule comprising a nucleic acid sequence coding for an antibody as described above, a recombinant nucleic acid molecule comprising a nucleic acid sequence coding for a component part of an antibody as described above, a recombinant nucleic acid molecule, wherein transcription of the antibody coding sequence is under a control of a transcriptional promoter effective in a suitable host cell, a recombinant nucleic acid molecule as herein described, further comprising a nucleic acid sequence encoding an in frame signal peptide suitable to promote secretion of the translated antibody. The recombinant nucleic acid molecule according to the present invention preferably further comprises a selection marker suitable for selecting host cells expressing the marker. It can be a deoxyribonucleic acid molecule or a ribonucleic acid molecule in the forms of, where applicable, for example, a naked nucleic acid molecule, a phage vector, a plasmid vector, a cosmid vector, a shuttle vector, a viral vector and a yeast artificial chromosome.

The host cell producing the antibody can be a eukaryotic host cell and a prokaryotic host cell. The eukaryotic host cell can be an animal cell, a plant cell, a fungal cell or a yeast cell. Preferably, the eukaryotic host cell is a plant cell.

Further according to the present invention there are provided genetically modified cells or plants transfected with the recombinant nucleic acid described herein; genetically modified cells or plants expressing the recombinant nucleic acid described herein; genetically modified cells or plants expressing the recombinant nucleic acid described herein; genetically modified cells or plants producing a catalytic antibody as described herein; and genetically modified cells or plants producing a component part of a catalytic antibody as described herein.

Further according to the present invention there are provided immunocytes immortalized immunocytes producing a catalytic antibody as described herein.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A catalytic antibody that is capable of catalyzing the deactivation of a precursor in the synthetic pathway of ethylene in plants, so as to deplete the precursor from the metabolic pool, the catalytic antibody comprising an immunoglobulin that binds a stable transition state analog of a deactivation reaction of the precursor.

2. The catalytic antibody of claim 1, wherein the precursor is selected from the group consisting of 1-aminocyclopropane-1-carboxylic acid and S-adenosyl methionine.

3. The catalytic antibody of claim 1, wherein the precursor is 1-aminocyclopropane-1-carboxylic acid and said stable transition state analog is selected from the group consisting of:

and wherein X is selected from the group consisting of N atom or P atom;

Cn is an integral number of carbon atoms from 1 to 5;

Cm is an integral number of carbon atoms from 1 to 3; and m is an integer selected from 1–3; and R is selected from the group consisting of an alkyl group and O—, wherein X is selected from the group consisting of N atom or P atom;

n is an integer selected from 1–5;

m is an integer selected from 1–3; and

R is selected from the group consisting of an alkyl group and O—.

4. The catalytic antibody of claim 1, wherein said deactivation is effected by decomposition.

5. The catalytic antibody of claim 4, wherein said decomposition is hydrolysis of a carbon—carbon bond.

6. A component part of the antibody of claim 1, which is capable of catalyzing the deactivation of a precursor in the synthetic pathway of ethylene in plants, so as to deplete the precursor from the metabolic pool, said component part is selected from the group consisting of an F(abAE)2 fragment, an Fab fragment, an Fv fragment, a heavy chain, a light chain, an unassociated mixture of a heavy chain and a light chain, a heterodimer consisting of a heavy chain and a light chain, a catalytic domain of a heavy chain, a catalytic domain of a light chain, a variable fragment of a light chain, a variable fragment of a heavy chain, and a single chain variant of said antibody.

7. Immortalized immunocytes producing a catalytic antibody according to claim 1.

8. Immunocytes producing a catalytic antibody according to claim 1.

* * * * *

UNITED STATES PATENT AND TRADEMARK OFFICE
CERTIFICATE OF CORRECTION

PATENT NO. : 6,271,009 B1
DATED : August 7, 2001
INVENTOR(S) : Keinan et al.

It is certified that error appears in the above-identified patent and that said Letters Patent is hereby corrected as shown below:

Column 20, claim 6,
Line 31, there is a typographical error within the parenthesis at the end of the line "F(abAE)2" appears instead of -- F(ab')2 --

Signed and Sealed this

Second Day of April, 2002

Attest:

Attesting Officer

JAMES E. ROGAN
Director of the United States Patent and Trademark Office